ized Patent [19] 4,264,527
Curtis [45] Apr. 28, 1981

[54] PROCESS FOR THE PREPARATION OF CYCLOPROPYLMETHYL-N-PROPYLAMINE

[75] Inventor: Edwyn A. Curtis, Mobile, Ala.

[73] Assignee: Ciba-Geigy Corporation, Ardsley, N.Y.

[21] Appl. No.: 61,884

[22] Filed: Aug. 1, 1979

[51] Int. Cl.³ .............................................. C07C 83/00
[52] U.S. Cl. .................................................... 564/455
[58] Field of Search ..................................... 260/563 R

[56] References Cited

U.S. PATENT DOCUMENTS 3,739,025  6/1973  Linder et al. ................... 260/563 R
3,847,984  11/1974  Linder et al. ................... 260/563 R
3,847,985  11/1974  Linder et al. ................... 260/563 R Primary Examiner—Paul F. Shaver
Attorney, Agent, or Firm—Karl F. Jorda

[57] ABSTRACT

A process for preparing cyclopropylmethyl-n-propylamine from the reaction of cyclopropylmethylamine with propionitrile is described. The reaction takes place in the presence of a hydrogenation catalyst, preferably a mixture of rhodium on carbon and platinum on carbon. The process is particularly useful as it consumes the cyclopropylmethylamine by-product from another scheme for the synthesis of cyclopropylmethyl-n-propylamine.

22 Claims, No Drawings

PROCESS FOR THE PREPARATION OF CYCLOPROPYLMETHYL-N-PROPYLAMINE

FIELD OF THE INVENTION

This invention relates to a process for preparing cyclopropylmethyl-n-propylamine. More particularly the invention relates to reacting cyclopropylmethylamine (CPMA) with propionitrile (PB) in the presence of hydrogen and a hydrogenation catalyst, rhodium, palladium or platinum supported on carbon, and a mixture of rhodium supported on carbon and platinum supported on carbon.

BACKGROUND OF THE INVENTION

In U.S. Pat. No. 3,739,025, U.S. Pat. No. 3,847,984 and U.S. Pat. No. 3,847,985, methods for preparing cyclopropylmethyl-alkyl-amines are described including reacting cyclopropylmethylamine (CPMA) with ketones, aldehydes or alcohols in the presence of hydrogen and a metal hydrogenation catalyst or compound thereof. A representative equation is as follows:

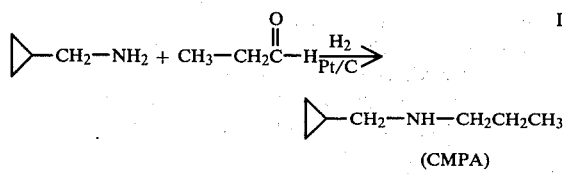

(CMPA)

The catalytic materials can be in pure form but preferably are deposited on a carrier, such as carbon, alumina, silica gel, barium sulfate, calcium carbonate, barium carbonate, kieselguhr, zirconia, thoria, magnesia, titania, montmorillonite clay, bauxite, diatomaceous earth, course porcelain or any other refractory material which has no adverse effect on the reaction.

Useful catalysts for these reactions are selected from the group consisting of rhodium on carbon, platinum on carbon, palladium on carbon, Raney nickel or nickel-cobalt, copper on a siliceous support, copper on alumina, or unsupported copper chromite which may contain 1-50% barium chromite.

THE INVENTION

It has now been found that by reacting cyclopropylmethylamine with propionitrile, a good yield of cyclopropylmethyl-n-propylamine can be obtained according to the following equation:

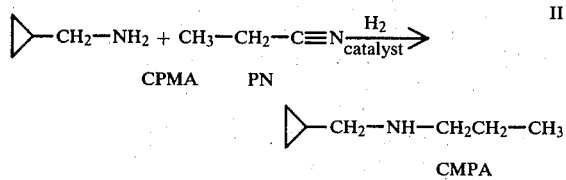

CMPA

The catalyst is selected from the group consisting of rhodium supported on carbon; platinum supported on carbon; palladium supported on carbon; and a mixture of rhodium supported on carbon and platinum supported on carbon. Very high yields of cyclopropylmethyl-n-propylamine (CMPA) are obtained amounting to 90%-100% based on the weight of cyclopropylmethylamine (CPMA).

In the mixed catalyst, which is preferred, the weight of platinum, based on the total weight of metal present in the catalyst, can be in the range of up to about 99%, advantageously in the range of about 25 to 75%, preferably in the range 50 to 67%, most preferably in the range of about 60 to 67%, optimally at about 60%. A mixed catalyst suitable for the process of this invention consists of a mixture of rhodium on carbon, with rhodium accounting for 1 to 12% by weight. The preferred mixed catalyst consists of a mixture of about 5% platinum on carbon in a 4:6 weight ratio. Other suitable catalysts are rhodium on carbon, palladium on carbon or platinum on carbon with the metal accounting for 1 to 12% by weight, preferably about 5% by weight of the catalyst. The weight of the catalyst used preferably amounts to about 0.5 to 0.6% by weight based on the weight of propionitrile.

The mole ratio in the reaction of cyclopropylmethylamine to propionitrile is in the range of about 5:1 to 1:1 preferably about 3:1 to 2:1 and optimally 2.35:1 to 3.0:1.

The reaction is carried out in hydrogen and under pressures of about 40 to 300 psig., preferably about 150 psig.

The reaction proceeds satisfactorily at temperatures in the range of 0° to 80° C. and especially at 40° C.

The reaction takes place in a mutual solvent for the amine and nitrile. Alkanols such as methanol are suitable solvents. The reaction also proceeds in the absence of a solvent. The latter condition is presently preferred.

The choice of the preferred catalyst is governed by the speed of the reaction, specificity of yield and overall yield as evidenced by the data in Table 1:

TABLE 1

| Catalyst | 40° C. Reaction Time | Yield Based on PN | Yield Based on CPMA |
|---|---|---|---|
| 5% Pd/C | 2.3 Hours | 53.4% | 98.8% |
| 5% Pt/C | 6.9 Hours (incomplete) | 36.4% | — |
| 5% RH/C | 3.75 Hours | 58.9% | 61.8% |
| 5% Pd/C | 6.25 Hours | 64.1% | 88.1% |
| (60%), 5% Rh/C (40%), 5% Pt/C 5.0 Hours | | 65.3% | 95.3% |

The specific catalyst was chosen based on the data in Table 2 below:

TABLE 2

| % RH | % Pt | 50° C. Reaction Time | Yield Based on PN | Yield Based on CMPA |
|---|---|---|---|---|
| 60 | 40 | 1.8 Hours | 60.1% | 97.3% |
| 50 | 50 | 1.4 Hours | 61.6% | 98.9% |
| 40 | 60 | 1.5 Hours | 60.5% | 98.2% |
| 33 | 67 | 1.3 Hours | 61.5% | 98.8% |
| 25 | 75 | 2.0 Hours | 61.1% | 96.0% |

From Table 2 it will be seen that the mixed catalysts containing 50 to 67% platinum provided the fastest reaction times and highest yields, substantially equivalent within experimental error. As the 60% platinum 40% rhodium mixture is less expensive it is the preferred catalyst.

The starting cyclopropylmethylamine is a by-product from the process for the preparation of cyclopropylmethyl-n-propylamine from cyclopropyl cyanide, also known as cyclopropylnitrile (CPN). This is an intermediate for the manufacture of certain herbicides. The major process proceeds is according to equation III:

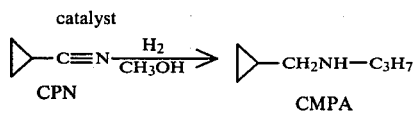

III but a side reaction provides cyclopropylmethylamine (CPMA) according to equation IV:

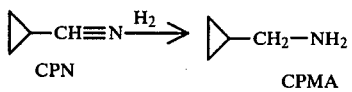

IV

This side reaction accounts for about 10 to 12% of the cyclopropyl cyanide (CPN) consumed in the general process of equation III.

The conversion of this by-product to the desired end product by the process of this invention thus provides an economically desirable utility particularly since it is more than 90% efficient based on the amount of the by-product processed.

EXAMPLE 1

57.4 g (96%/1 mole) of propionitrile, 6.35 g of 5% rhodium supported on carbon, 232.2 g (90.17%; 7.4% $H_2O$) of cyclopropylmethylamine and 151.1 g of methanol are fed into a 1-liter Parr hydrogenation apparatus. The reaction mixture is hydrogenated at about 40° C. Hydrogen is introduced under 145–150 psig hydrogen pressure. When the hydrogen is no longer absorbed, the temperature is increased to 60° C. and held about 1 hour 15 minutes. After cooling to room temperature, the mixture is filtered to remove the catalyst and to yield 429.4 g of filtrate, containing 16.1% (61.2% yield based on propionitrile) of cyclopropylmethyl-n-propylamine in methanol. This is recovered by distillation. BP 135°–148° C. The yield, based on the amount of cyclopropylmethylamine used, is 92.7%.

EXAMPLE 2

(Pilot Plant)

A 30 gallon jacketed stainless steel pressure vessel fitted with 5 gallon catalyst drop tank is purged with nitrogen and charged with 126 lbs (17.6 gallons) of a 55% solution of cyclopropylmethylamine in methanol recovered from a cyclopropyl cyanide (CPN) catalytic hydrogenation. To this is added 48.5 lbs of methanol (7.4 gallons) and the temperature is controlled to the range 20°–25° C.

The nitrogen-purged drop tank is charged with 12.5 lbs of a 60-40 mixture of 5% Pt/C and 5% Rh/C catalyst and 13 lbs (2 gallons) of propionitrile (96% pure). The catalyst is slurried by agitation and dropped into the main vessel. An additional 11 lbs (17 gal) of propionitrile is used to flush any slurry residue into the vessel which is then purged of $O_2$ with nitrogen. The mole ratio of propionitrile to cyclopropylmethylamine is 1:2.35. When the $O_2$ level is below 0.5%, the vessel is pressurized to 150 psig with hydrogen. The vessel temperature is maintained at 50°±2° C. and additional hydrogen is added as consumed to maintain the pressure. WHen the hydrogen uptake ceases, the reaction mixture is heated to 60° C. and held there for 2 hours. The mixture is then cooled to 20° C., the hydrogen is carefully vented and the vessel is flushed with nitrogen. The reaction mass is filtered to remove the catalyst and the filtrate is distilled. 28.1 lbs of cyclopropylmethyl-n-propylamine is recovered in 90% yield, based on the cyclopropylmethylamine content of the starting material and 60% yield based on propionitrile.

EXAMPLE 3

Plant

A 3000 gallon stainless steel reactor assembly fitted with a 500 gallon drop tank purged with nitrogen. The drop tank is charged with 50 lbs of 5% rhodium on carbon catalyst and 75 lbs of 5% platinum on carbon catalyst, and 200 gallons (1,288 lbs) of propionitrile (99.9%). This mixture is agitated for 10 minutes.

The reactor is meanwhile charged with 2,200 gallons (15,380 lbs) of cyclopropylmethylamine (71–72% purity recovered from the production process according to equation III and formed by side reaction IV). The cyclopropylmethylamine in the reactor is agitated and its temperature stabilized to 18° C. The residual purge nitrogen is vented and the slurry from the drop tank is introduced into the reactor. An additional 242 gallons (1,560 lbs) of propionitrile is used to flush the residual catalyst from the drop tank into the reactor. The reactor is then again purged with nitrogen until the oxygen content of the flushed gas is below 0.5 volume %.

The reactor is then pressurized with hydrogen to 150 psig. The hydrogen feed is continued to maintain the 150 psig until hydrogen uptake ceases, while maintaining the temperature within the reactor at about 50°–60° C. The hydrogen uptake ceases after about 7 to 8 hours. The hydrogen feed is shut off and the reactor temperature is held at 60° C. for two hours.

The hydrogen pressure is then reduced to 5 psig. The residual hydrogen is purged from the reactor by a flow of nitrogen.

The contents from the reactor are then filtered to remove the catalyst residue and the filtrate is worked up by distillation.

Yield: Total cyclopropylmethylpropylamine (3,512 lbs). 60% cyclopropylmethylpropylamine based on propionitrile 90% cyclopropylmethylpropylamine based on cyclopropylmethylamine.

What is claimed is:

1. A process for preparing cyclopropylmethyl-n-propylamine comprising the step of reacting cyclopropylmethylamine with propionitrile in the presence of hydrogen and a catalyst selected from the group consisting of rhodium supported on carbon, palladium supported on carbon, platinum supported on carbon, or a mixture of rhodium supported on carbon and platinum supported on carbon.

2. The process according to claim 1, wherein a catalyst consisting of a mixture of rhodium supported on carbon and platinum supported on carbon is employed, said catalyst containing 25 to 75% by weight of platinum based on the total weight of metal in the catalyst.

3. The process according to claim 2, wherein the catalyst contains 50 to 67% by weight of platinum based on the total weight of metal present in the catalyst.

4. The process according to claim 3, wherein the catalyst contains 60 to 67% by weight of platinum based on the total weight of metal present in the catalyst.

5. The process according to claim 4, wherein the catalyst contains 60% by weight of platinum based on the total weight of metal present in the catalyst.

6. The process according to claim 1, wherein a catalyst consisting of a mixture of 1–12% by weight of platinum supported on carbon and 1–12% rhodium supported on carbon is employed.

7. The process according to claim 6, wherein a catalyst consisting of a mixture of 5% by weight of platinum supported on carbon and 5% of rhodium supported on carbon is employed.

8. The process according to claim 1, wherein the mole ratio of cyclopropylmethylamine to propionitrile is in the range about 5:1 to 2:1.

9. The process according to claim 8, wherein the mole ratio of cyclopropylmethylamine to propionitrile is substantially 2.35:1 to 3.0:1.

10. The process according to claim 1, wherein the catalyst amounts to about 0.5 to 0.6% by weight based on the weight of propionitrile.

11. The process according to claim 1, wherein the reaction is carried out at a pressure range of about 40 to 300 psig.

12. The process according to claim 11, wherein the reaction is carried out at a pressure of about 150 psig.

13. The process according to claim 1, wherein the process is carried out at a temperature of about 10° to 80° C.

14. The process according to claim 13 wherein the process is carried out at a temperature of about 50° C.

15. The process according to claim 1 wherein the catalyst consists of rhodium.

16. The process according to claim 15 wherein the catalyst consists of 5% rhodium supported on carbon.

17. The process according to claim 1 wherein the catalyst consists of platinum.

18. The process according to claim 17 wherein the catalyst consists of 5% platinum supported on carbon.

19. The process according to claim 1 wherein the catalyst consists of palladium.

20. The process according to claim 19 wherein the catalyst consists of 5% palladium supported on carbon.

21. The process according to claim 1 wherein the process is carried out in a mutual solvent of the cyclopropylmethylamine and the propionitrile.

22. The process according to claim 20 wherein the solvent is methanol.

* * * * *